(12) United States Patent
Hayes

(10) Patent No.: US 10,272,129 B1
(45) Date of Patent: Apr. 30, 2019

(54) OINTMENT

(71) Applicant: Deborah L. Hayes, Memphis, TN (US)

(72) Inventor: Deborah L. Hayes, Memphis, TN (US)

( * ) Notice: Subject to any disclaimer, the term of this patent is extended or adjusted under 35 U.S.C. 154(b) by 0 days.

(21) Appl. No.: 15/825,060

(22) Filed: Nov. 28, 2017

(51) Int. Cl.
| | |
|---|---|
| *A61K 36/889* | (2006.01) |
| *A61K 36/71* | (2006.01) |
| *A61K 9/06* | (2006.01) |
| *A61P 17/02* | (2006.01) |
| *A61K 36/185* | (2006.01) |
| *A61K 36/282* | (2006.01) |
| *A61K 36/30* | (2006.01) |
| *A61K 36/49* | (2006.01) |
| *A61K 36/56* | (2006.01) |
| *A61K 36/80* | (2006.01) |
| *A61K 36/52* | (2006.01) |
| *A61K 33/06* | (2006.01) |
| *A61K 36/28* | (2006.01) |
| *A61K 36/539* | (2006.01) |
| *A61P 29/00* | (2006.01) |

(52) U.S. Cl.
CPC ............. *A61K 36/889* (2013.01); *A61K 9/06* (2013.01); *A61K 33/06* (2013.01); *A61K 36/185* (2013.01); *A61K 36/28* (2013.01); *A61K 36/282* (2013.01); *A61K 36/30* (2013.01); *A61K 36/49* (2013.01); *A61K 36/52* (2013.01); *A61K 36/539* (2013.01); *A61K 36/56* (2013.01); *A61K 36/71* (2013.01); *A61K 36/80* (2013.01); *A61P 17/02* (2018.01); *A61P 29/00* (2018.01)

(58) Field of Classification Search
CPC ........ A61K 36/889; A61K 9/06; A61K 33/06; A61K 36/185; A61K 36/28; A61K 36/282; A61K 36/30; A61K 36/49; A61K 36/80; A61K 36/539; A61K 36/52; A61K 36/56; A61K 36/71; A61P 17/02; A61P 29/00

See application file for complete search history.

(56) References Cited

U.S. PATENT DOCUMENTS

2006/0269507 A1* 11/2006 Fuller .................. A61K 8/922
424/74

* cited by examiner

*Primary Examiner* — Blessing M Fubara
(74) *Attorney, Agent, or Firm* — David J. Kreher

(57) ABSTRACT

A method of making an ointment that begins to work on contact, is all-natural and organic, is an anti-inflammatory ointment for pain relief and wound healing, which is to be applied to the skin. Further claimed is ointment produced by said method.

2 Claims, No Drawings

OINTMENT

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC

Not Applicable

DESCRIPTION

Field of the Invention

This invention relates to a fast-acting, all-natural, organic, anti-inflammatory ointment for pain relief and wound healing, which is applied to the skin.

Background of the Invention

Many drugs have been developed to treat pain relief associated with muscle aches as well as diabetic nerve pain, headaches, chronic itching, psoriasis, eczema, and cystic acne pain. The present disclosure reveals a method of manufacture and ointment that begins to act on contact, is all-natural and organic, is an anti-inflammatory, and is for pain relief and wound healing, which is applied to the skin.

AMENDED SUMMARY OF THE INVENTION

The present disclosure claims a method of manufacture of an ointment as well as the ointment that begins to act on contact, is all-natural and organic, is an anti-inflammatory ointment for pain relief and wound healing, which is applied to the skin. The ointment is consisting of:
Coconut oil
Sweet Weed (*Aethaea Officinalis*)
Green Ginger (*Artemisia Absinthium*)
Indian Pink (*Spigelia Merilandica*)
Slippery Root (*Symphytum Officinale*)
Velvet Plant (*Verbascum Thapsus*)
American Walnut (*Juglans Nigra*)
Tanner's Bark (*Quercus Robur*)
Magnesium Flakes
Gravel Root (*Eutrochium Purpureum*)
Mad Dog Weed (*Scutellaria Lateriflora*)
Nigella Seed (*Nigella Sativa*)
The method of manufacture involves combining the ingredients, simmering for 4 to 8 hours at between 170 and 200 degrees, and straining the compound to extract the ointment from the residue.

AMENDED DESCRIPTION OF THE SEVERAL VIEWS OF THE DRAWING

Not Applicable

AMENDED DETAILED DESCRIPTION OF THE INVENTION

The present disclosure reveals a method of making an ointment consisting of:
an ointment being an anti-inflammatory ointment for pain relief and wound healing, wherein the ointment begins to work on contact, is all-natural and organic, and is to be applied to the skin.

The method of manufacture consisting of combining the following ingredients based on weight percentage into a mixture:

| Ingredient | Amount (Weight Percentage) |
|---|---|
| Coconut oil | 88.95-90.29 |
| Sweet Weed (Aethaea Officinalis) | 0.98-1.14 |
| Green Ginger (Artemisia Absinthium) | 0.60-0.70 |
| Indian Pink (Spigelia Merilandica) | 0.60-0.70 |
| Slippery Root (Symphytum Officinale) | 1.96-2.16 |
| Velvet Plant (Verbascum thapsus) | 0.98-1.02 |
| American Walnut husks (Juglans nigra) | 0.98-1.02 |
| Tanner's Bark (Quercus Robur) | 1.96-2.16 |
| Magnesium Flakes | 0.15-0.25 |
| Gravel Root (Eutrochium Purpureum) | 0.90-1.02 |
| Mad Dog Weed (Scutellaria Lateriflora) | 0.30-0.44 |
| Nigella Seed (Nigella Sativa) | 0.30-0.44 |

Any deficiency in percentage would result in the inclusion of additional coconut oil.

Once combined into a mixture, simmering said mixture for 4 to 8 hours, then straining the mixture to separate out the ointment from the residue.

Applicant further claims the ointment produced from the above described method.

What is claimed:

1. A method of making an anti-inflammatory ointment consisting of:
an anti-inflammatory ointment for pain relief and wound healing, from a collection of ingredients that are all-natural and organic, wherein the ointment begins to act on contact, and wherein said ointment is to be applied to the skin
the method of making said ointment consisting of:
combining the following ingredients identified by weight percentage into a mixture;

| | |
|---|---|
| coconut oil | 88.95-90.29; |
| sweet weed (aethaea officinalis) | 0.98-1.14; |
| green ginger (artemisia absinthium) | 0.60-0.70; |
| indian pink (spigelia merilandica) | 0.60-0.70; |
| slippery root (symphytum officinale) | 1.96-2.16; |
| velvet plant (verbascum thapsus) | 0.98-1.02; |
| american walnut husks (juglans nigra) | 0.98-1.02; |
| tanner's bark (quercus robur) | 1.96-2.16; |
| magnesium flakes | 0.15-0.25; |
| gravel root (eutrochium purpureum) | 0.90-1.02; |
| mad dog weed (scutellaria lateriflora) | 0.30-0.44; |
| nigella seed (nigella sativa) | 0.30-0.44; | any deficiency in content to be comprised of additional coconut oil;
simmering said mixture for 4 to 8 hours to extract oils contained in the ingredients into the coconut oil to produce an ointment and to produce a residue; and
straining the mixture to separate out the ointment from the residue.

2. The ointment of claim 1, said ointment being an all-natural and organic anti-inflammatory ointment to be used for pain relief and wound healing, wherein the ointment begins to act on contact, and wherein said ointment is to be applied to the skin.

* * * * *